US00PP24240P2

(12) United States Plant Patent
Hooijman

(10) Patent No.: US PP24,240 P2
(45) Date of Patent: Feb. 11, 2014

(54) *GYPSOPHILA* PLANT NAMED 'ESM G007'

(50) Latin Name: ***Gypsophila paniculata*×*Gypsophila porrigens***
Varietal Denomination: Esm G007

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 94 days.

(21) Appl. No.: 13/506,272

(22) Filed: Apr. 7, 2012

(51) Int. Cl.
*A01H 5/00* (2006.01)

(52) U.S. Cl.
USPC ..... Plt./354

(58) Field of Classification Search
USPC ..... Plt./354
See application file for complete search history.

*Primary Examiner* — Susan McCormick Ewoldt
(74) *Attorney, Agent, or Firm* — C. A. Whealy

(57) ABSTRACT

A new and distinct cultivar of *Gypsophila* plant name 'Esm G007', characterized by its erect, straight and moderately strong flowering stems; uniform and freely flowering habit; compact and dense inflorescences with luminous white-colored flowers; and good postproduction longevity.

1 Drawing Sheet

Botanical designation: *Gypsophila paniculata*×*Gypsophila porrigens*.

Cultivar denomination: 'ESM G007'.

BACKGROUND OF THE INVENTION

The present invention relates to a new and distinct cultivar of *Gypsophila* plant, botanically known as *Gypsophila paniculata*×*Gypsophila porrigens*, grown commercially as a cut flower, and hereinafter referred to by the name 'Esm G007'.

The new *Gypsophila* plant is a product of a planned breeding program conducted by the Inventor in El Quinche, Pichincha, Ecuador. The objective of the breeding program is to create new productive *Gypsophila* plants with numerous flowers and good postproduction longevity.

The new *Gypsophila* plant originated from a cross-pollination conducted by the Inventor in El Quinche, Pichincha, Ecuador in August, 2007 of a proprietary selection of *Gypsophila paniculata* identified as Line 252, not patented, as the female, or seed, parent with a proprietary selection of *Gypsophila porrigens* identified as Line 337, not patented, as the male, or pollen, parent. The new *Gypsophila* plant was discovered and selected by the Inventor as a single flowering plant from within the progeny of the stated cross-pollination in a controlled environment in El Quinche, Pichincha, Ecuador in February, 2008.

Asexual reproduction of the new *Gypsophila* plant by cuttings in a controlled environment in El Quinche, Pichincha, Ecuador since April, 2008 has shown that the unique features of this new *Gypsophila* plant are stable and reproduced true to type in successive generations.

SUMMARY OF THE INVENTION

Plants of the new *Gypsophila* have not been observed under all possible environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Esm G007'.

These characteristics in combination distinguish 'Esm G007' as a new and distinct *Gypsophila* plant:

1. Erect, straight and moderately strong flowering stems.
2. Uniform and freely flowering habit.
3. Compact and dense inflorescences with luminous white-colored flowers.
4. Good postproduction longevity.

In side-by-side comparisons conducted in El Quinche, Pichincha, Ecuador, plants of the new *Gypsophila* differed from plants of the female parent selection in the following characteristics:

1. Plants of the new *Gypsophila* had moderately strong flowering stems whereas plants of the female parent selection had strong flowering stems.
2. Flower form of plants of the new *Gypsophila* was semi-double whereas flower form of plants of the female parent selection was double.

In side-by-side comparisons conducted in El Quinche, Pichincha, Ecuador, plants of the new *Gypsophila* differed from plants of the male parent selection in the following characteristics:

1. Plants of the new *Gypsophila* were taller than plants of the male parent selection.
2. Plants of the new *Gypsophila* had denser inflorescences than plants of the male parent selection.
3. Flowers of plants of the new *Gypsophila* had more petals than flowers of plants of the male parent selection.
4. Flower color of plants of the new *Gypsophila* was more luminous than flower color of plants of the male parent selection.

Plants of the new *Gypsophila* can also be compared to plants of the *Gypsophila* 'Esmamerica', disclosed in U.S. Plant Pat. No. 14,940. In side-by-side comparisons conducted in El Quinche, Pichincha, Ecuador, plants of the new *Gypsophila* differed from plants of 'Esmamerica' in the following characteristics:

1. Plants of the new *Gypsophila* were shorter and broader than plants of 'Esmamerica'.
2. Plants of the new *Gypsophila* were not as vigorous as plants of 'Esmamerica'.

3. Inflorescences of plants of the new *Gypsophila* were larger and denser than inflorescences of plants of 'Esmamerica'.
4. Plants of new *Gypsophila* were more freely flowering than plants of 'Esmamerica'.

BRIEF DESCRIPTION OF THE PHOTOGRAPH

The accompanying photograph illustrates the overall appearance of the new *Gypsophila* plant showing the colors as true as it is reasonably possible to obtain in colored reproductions of this type. Colors in the photograph may differ slightly from the color values cited in the detailed botanical description which accurately describe the colors of the new *Gypsophila* plant. The photograph comprises a side perspective view of a typical flowering stem of 'Esm G007' (upper left); close-up view of a typical inflorescence of 'Esm G007' (upper right); close-up view of a typical flower of 'Esm G007' (lower left); and close-up view of upper and lower surfaces of typical leaves of 'Esm G007' (lower right).

DETAILED BOTANICAL DESCRIPTION

The aforementioned photograph and following observations and measurements describe plants grown in ground beds in an outdoor nursery in El Quinche, Pichincha, Ecuador and under cultural practices which approximate those generally used in commercial cut *Gypsophila* production. During the production of the plants, day temperatures ranged from 11° C. to 28° C. and night temperatures ranged from 5° C. to 11° C. Plants were pinched one time five weeks after planting and five weeks after pinching, plants were grown under long day/short day conditions. Measurements and numerical values represent averages for typical 44-week old flowering plants. In the following description, color references are made to The Royal Horticultural Society Colour Chart, Fourth Edition, 2001, except where general terms of ordinary dictionary significance are used.

Botanical classification: *Gypsophila paniculata*×*Gypsophila porrigens* 'Esm G007'.

Commercial classification: Cut flower *Gypsophila*.

Parentage:

*Female, or seed, parent*.—Proprietary selection of *Gypsophila paniculata* identified as Line 252, not patented.

*Male, or pollen, parent*.—Proprietary selection of *Gypsophila porrigens* identified as Line 337, not patented.

Propagation:

*Type*.—By cuttings.

*Time to initiate roots, summer*.—About 16 to 21 days at 17° C. to 25° C.

*Time to produce a rooted young plant, summer*.—About five to six weeks at 17° C. to 25° C.

*Root description*.—Medium in thickness, fibrous; close to 199A in color.

*Rooting habit*.—Freely branching; medium density.

Plant description:

*Appearance*.—Perennial cut flower; erect and moderately strong flowering stems; inverted triangle form; uniform and freely flowering habit; luminous white-colored flowers; moderately vigorous growth habit.

*Branching habit*.—When pinched, about 17.5 flowering stems develop per year.

*Plant height*.—About 108 cm.

*Plant diameter or spread*.—About 72 cm.

*Flowering stems*.—Length: About 96 cm. Diameter: About 4 mm. Internode length: About 5.2 cm. Strength: Moderately strong. Texture: Glabrescent. Color: Close to 146A.

Foliage description:

*Arrangement*.—Opposite, decussate, simple; sessile.

*Length*.—About 7 cm.

*Width*.—About 1.1 cm.

*Shape*.—Lanceolate.

*Apex*.—Acute.

*Base*.—Cuneate.

*Margin*.—Entire.

*Texture, upper and lower surfaces*.—Smooth, glabrous; waxy.

*Venation pattern*.—Parallel.

*Color*.—Developing leaves, upper and lower surfaces: Between 147A and 139A. Fully expanded leaves, upper surface: Between 147A and 139A; venation, between 147A and 139A. Fully expanded leaves, lower surface: Close to 147A; venation, close to 146A.

Flower description:

*Flower arrangement and habit*.—Symmetrical and uniform compound cymes with numerous luminous white-colored flowers, flowers rotate; freely flowering habit, about 2,000 flowers per inflorescence; flowers face mostly upright.

*Flowering response*.—In Ecuador, plants flower year round; early flowering habit; plants begin flowering about 16 weeks after planting.

*Post-production longevity*.—As a cut flower, flowers last for about nine days; on the plant, flowers last for about 12 to 14 days; flowers persistent.

*Fragrance*.—Slightly fragrant; pleasant.

*Inflorescence height*.—About 70 cm.

*Inflorescence diameter*.—About 43 cm.

*Flower diameter*.—About 7 mm.

*Flower depth (height)*.—About 6 mm.

*Flower buds*.—Length: About 2 mm. Diameter: About 2 mm. Shape: Nearly globose. Color: Close to 146A and 145D.

*Petals*.—Quantity per flower: About 30 fused at the base in clusters. Length: About 4 mm. Width: About 2 mm. Shape: Oval to spatulate. Apex: Truncate, emarginate or obtuse. Margin: Entire. Texture, upper and lower surfaces: Smooth, glabrous; waxy. Color: When opening and fully opening, upper surface: Close to 155C; towards the base, close to 145C; color becoming closer to 161 C with development. When opening and fully opening, lower surface: Close to 155C; towards the base, close to 145C; color becoming closer to 161 C with development.

*Sepals*.—Quantity per flower: About five fused to form a cupped star-shaped calyx. Length: About 2.5 mm. Width: About 1.5 mm. Shape: Roughly lanceolate. Apex: Acute. Margin: Entire. Texture, upper and lower surfaces: Glabrous, rough, membranous. Color: When developing, upper and lower surfaces: Close to 137A; center, close to 187A; towards the margins, close to 155C. Fully developed, upper surface: Close to 147A; towards the margins, close to 155C. Fully developed, lower surface: Close to 137A; center, close to 187A; towards the margins, close to 155C.

*Peduncles*.—Length: About 3.75 cm. Diameter: About 5.2 mm. Strength: Strong. Angle: About 27° from vertical. Texture: Smooth, glabrous. Color: Close to 146A.

*Pedicels*.—Length: About 7.4 mm. Diameter: About 0.4 mm. Strength: Moderately strong. Angle: About 39° from vertical. Texture: Smooth, glabrous. Color: Between 146A and 147A.

*Reproductive organs*.—Stamens: None observed. Pistils: Quantity per flower: One. Pistil length: About 5.1 mm. Style length: About 4.2 mm. Style color: Close to 155C. Stigma shape: Curved apiculate. Stigma color: Close to 155C. Ovary color: Close to 144B; towards the apex, close to N199B. Seeds and fruits: Seed and fruit production has not been observed on plants of the new *Gypsophila*.

Disease & pest resistance: Plants of the new *Gypsophila* have not been shown to be resistant to pathogens and pests common to *Gypsophila* plants.

Temperature tolerance: Plants of the new *Gypsophila* have been observed to tolerate temperatures ranging from about 7° C. to about 30° C.

It is claimed:

1. A new and distinct *Gypsophila* plant named 'Esm G007' as illustrated and described.

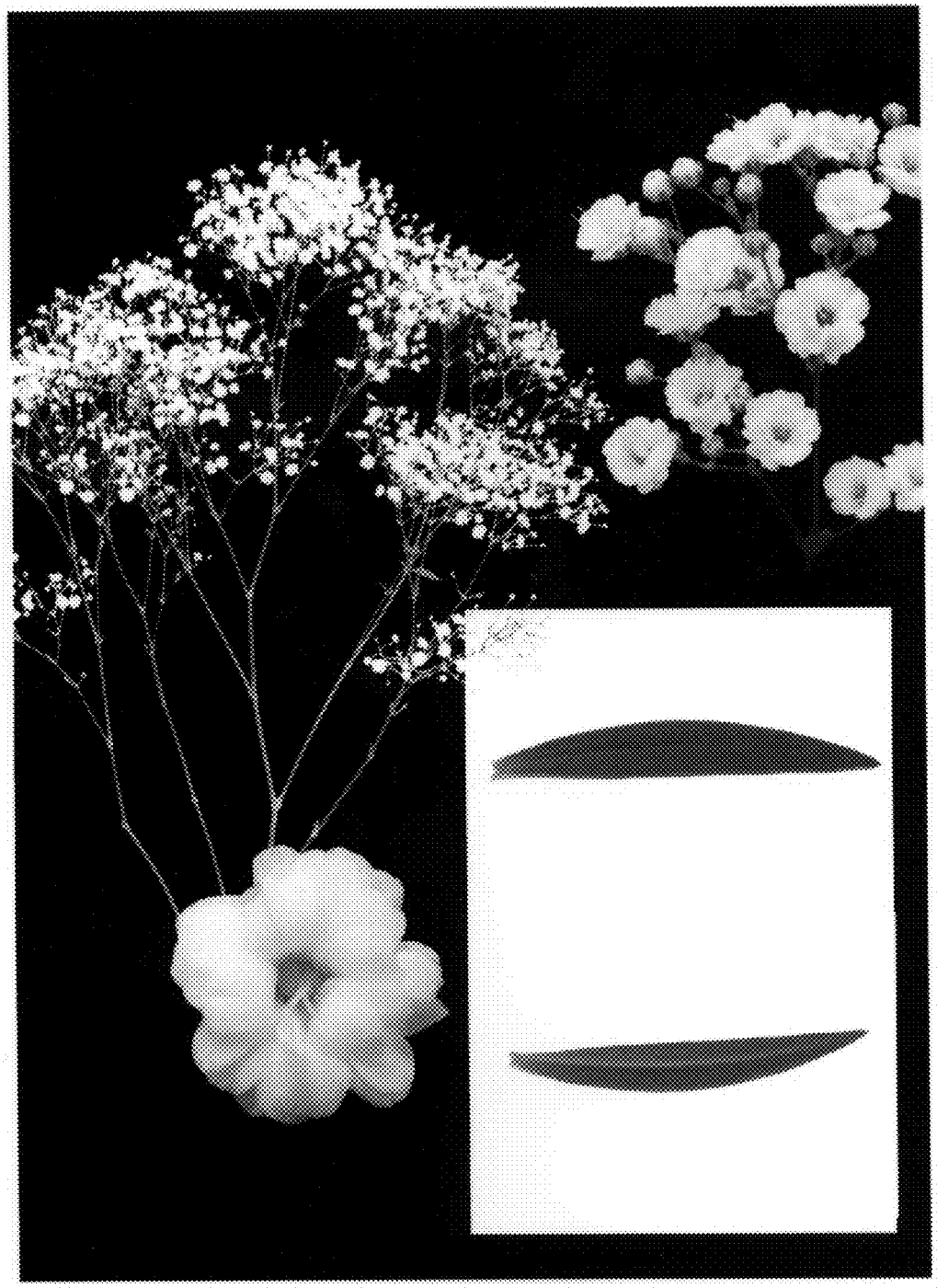

* * * * *